United States Patent [19]

Delacroix et al.

[11] Patent Number: 5,128,270
[45] Date of Patent: Jul. 7, 1992

[54] ASSAY OF MONOKINES

[75] Inventors: Dominique Delacroix, Kraainem; Donat De Groote, Waterloo; Paul Franchimont, Modave; Philippe Gysen, Neupre; Aimee Reuter, Liege; Isabelle Dehart, Brussels, all of Belgium

[73] Assignee: Ire-Medgenix S.A., Fleurus, Belgium

[21] Appl. No.: 299,803

[22] PCT Filed: May 18, 1988

[86] PCT No.: PCT/EP88/00430

§ 371 Date: Jan. 6, 1989

§ 102(e) Date: Jan. 6, 1989

[87] PCT Pub. No.: WO88/09508

PCT Pub. Date: Dec. 1, 1988

[30] Foreign Application Priority Data

May 19, 1987 [FR] France ............................ 87 06988

[51] Int. Cl.$^5$ ..................................... G01N 33/543
[52] U.S. Cl. .................................. 436/518; 436/504; 436/548; 436/18; 436/174; 436/804; 436/826; 435/7.24; 435/962; 435/968; 424/85.2; 424/85.7
[58] Field of Search ............... 435/7.24, 172.2, 240.67, 435/962, 968, 174; 436/503, 504, 518, 524, 527, 531, 547, 548; 424/1.1, 85.8, 85.2, 85.1; 530/351, 387

[56] References Cited

U.S. PATENT DOCUMENTS

| 4,302,437 | 11/1981 | Herbert. | |
|---|---|---|---|
| 4,376,110 | 3/1983 | David et al. | 436/513 |
| 4,434,236 | 2/1984 | Freytag | 436/512 |
| 4,514,505 | 4/1985 | Canfield et al. | 436/500 |
| 4,784,946 | 11/1988 | Mitsuhashi | 435/29 |
| 4,929,443 | 5/1990 | Lindblom et al. | 424/85.8 |

FOREIGN PATENT DOCUMENTS 0218531 10/1986 European Pat. Off. .
0220063 10/1986 European Pat. Off. .

OTHER PUBLICATIONS

Meager et al., "Preparation and Characterization of Monoclonal Antibodies Directed Against Antigenic Determinants of Recombinant Human Tumour Necrosis Factor" Hybridoma 6(3) pp. 305-311, Jun. 1987.

Lisi et al., "Development and Use of a Radioimmunoassay for Human Interleukin-1$\beta$" Lymphokine Research 6(3) pp. 229-244 Sep. 1987.

Gaffney et al., "Enzyme Linked Immunoassay with Monoclonal Antibody for Human Interleukin-1$\beta$" Biotechniques 5(7) pp. 652-657, Oct. 1987.

Kenney et al., "Monoclonal Antibodies to Human Recombinant Interleukin 1$\beta$-Quantitation of IL 1$\beta$ and Inhibition of Biological Activity" J. Immunol. 138(12) pp. 4236-4242 Jun. 15, 1987.

Lyte, Journal of Clinical Laboratory Analysis (1987) 1:83-88.

Gearing et al., Journal of Immunological Methods (1985) 83:1-3,27.

Kornbluth and Edgington, the Journal of Immunology (1986) 137:2585-2591.

Peters et al., The Journal of Immunology (1986) 137:2592-2598.

Primary Examiner—Esther L. Kepplinger
Assistant Examiner—Carol E. Bidwell
Attorney, Agent, or Firm—Cooley Godward Castro Huddleson & Tatum

[57] ABSTRACT

The invention relates to assays of a monokine in a biological fluid, in particular in a blood sample, in particular of TNF or of IL-1. According to the present invention, the monokine in the serum or plasma obtained from whole blood stimulated with a mitogenic agent is assayed prior to any separation between the plasma (or serum) and the blood cells. According to another subject of the invention, the monokine is assayed in the case of an immunometric assay employing an oligoclonal system, consisting of several different monoclonal antibodies adsorbed on a solid phase and a non-adsorbed labeled antibody.

The invention also relates to immunoassay kits.

16 Claims, 7 Drawing Sheets

ASSAY OF MONOKINES

The present invention relates, in a general manner, to assays of monokines. More specifically, the present invention relates to the assay of endogenous monokines in a biological fluid, in particular a blood sample.

Monokines belong to the group of cell mediators known as cytokines. Among cytokines, there are distinguished, in effect;

lymphokines, soluble mediators secreted by lymphocytes and activating either macrophages or other lymphocytes, and monokines, mediators secreted by monocytes or macrophages and acting either on cells of the lymphocytic line or on cells of mesenchymal origin.

The monokines to which the present invention relates consist, in particular, of tumor necrosis factor (TNF$\alpha$) and interleukin-1 (IL-1$\beta$). These two cell mediators are, in effect, known to have marked similarities in their behavior, such as their kinetics of release, or in their biological action ((1) see bibliographic references).

Apart from their aspect of anticancer or antiviral factors, it is known that TNF$\alpha$ and IL-1$\beta$ are secreted in different pathological conditions, especially, as regards TNF$\alpha$, in inflammatory states and during septic and pancreatic shock. More generally speaking, the secretion of TNF$\alpha$ and IL-1$\beta$ discloses a macrophage activation. Accordingly, the possibility of following this secretion of TNF$\alpha$ or of IL-1$\beta$ by a simple, reliable and rapid assay can be a source of very enlightening information concerning the functional aspect of macrophages in many pathological situations.

When the immunoassay of cytokines in a blood sample is contemplated, certain problems are encountered. Often, the sensitivity of the assays is regarded as insufficient for detecting these mediators directly in plasma or in blood serum, the quantities present to be assayed being too small. The problem can also arise from the nature of the values obtained, utilizable only with difficulty, where appropriate, the serum or plasma values varying little or in a non-significant manner from subject to subject, or between healthy subjects and sick subjects. This applies especially to lymphokines (IFN$\gamma$ (2) and IL-2 (3 a-b)).

As regards TNF$\alpha$, as will be seen later, (Example V: Clinical assessment), RIA immunoassay, which is, however, very sensitive, does not permit the direct detection in plasma of concentrations below 20 pg/ml, even with assay incubation times of 24 hours. Furthermore, if this time is reduced to 4 hours, which is more in accordance with practical requirements, this concentration detection limit rises to approximately 100 pg/ml.

As regards IRMA assays, which require incubations of only 2 hours, they do not, however, permit the direct detection of the presence of monokines in plasma.

The concentrations of TNF$\alpha$, obtained by direct RIA assay in plasma, are on average of the order of 50 pg/ml for healthy subjects, and do not exceed 200 pg/ml in most pathological conditions. These direct RIA assays in plasma are, however, utilizable only with difficulty.

In effect, values are obtained which vary little from one subject to another, even if the difference may be significant between a healthy subject and a subject suffering from a pathological condition in some cases. In addition, it is generally considered that the quantities to be assayed must be markedly greater (4- to 5-fold at least) than the detection limit value of the assay in order to offer a satisfactory discrimination of assaying, that is to say the possibility of large variations from subject to subject. These two conditions are hence not complied with.

Traditionally, the solution has consisted in assaying the cytokines in a blood sample by resorting to a stage of cell culturing in order to stimulate cytokine secretion ((2) IFN$\gamma$, (3 a-b) IL-2, (4) TNF$\alpha$, (5) IL-1).

The assays then consist in assaying the release of cytokines into culture media stimulated by the addition of a mitogenic agent, for example in assaying monokines on the supernatant of monocytes of peripheral blood cultured in the presence of a mitogenic agent. Values of the order of one nanogram per ml are then attained in the case of TNF$\alpha$(see Example V), that is to say concentrations markedly greater than the detection limit of the assays and showing large variations from one subject to another, especially when normal subjects and subjects suffering from pathological conditions are compared.

However, it is obvious that this practice of resorting to a stage of cell culturing is an unsatisfactory solution, in particular from the standpoint of application of the assay in routine clinical practice. The culturing stage gives rise, in effect, to certain variations which affect the reliability of the assay, in particular its reproducibility from patient to patient on the one hand, but also from sampling to sampling for the same patient on the other hand, not to mention, in addition, the need for a culturing intrastructure (sic) and for conditions of sterility, or a rather long assay time.

An object of the present invention was hence to propose a method, in particular an immunological method, for assaying monokines in a blood sample, which is reliable and utilizable as regards the values obtained, but simple and easy to use in routine clinical practice.

At the origin of the present invention, it was discovered that monokines, such as TNF$\alpha$ or IL-1$\beta$, are secreted much more rapidly than the other cytokines into cell culture media (see FIGS. 1 and 2), to such an extent that, surprisingly and as a novel feature, the stage of culturing mononuclear cells of peripheral blood could be avoided for the assay of monokines, assaying plasma directly provided the latter is obtained from whole blood, stimulated using a mitogenic agent before any stage of separation between plasma (or serum) and blood cells.

The subject of the present invention is hence an assay of monokines in a blood sample, in particular of TNF$\alpha$ or of IL-1$\beta$, wherein the monokine is assayed directly in the serum or in the plasma, the latter being obtained from whole blood stimulated beforehand with a mitogenic agent before separation of the plasma or serum.

In a particular embodiment, the blood sample to be assayed is withdrawn onto an anticoagulant, for example EDTA, and then brought into contact with the mitogenic agent, for example PHA, and incubated as it is. At the end of this operation, the blood is clarified by centrifugation, the monokine being assayed in the plasma obtained.

The stimulation of whole blood can be carried out, in particular, with 0.02 to 50 $\mu$g/ml of phytohemagglutinin (PHA) or 10 to 200 $\mu$g/ml of lipopolysaccharide (LPS) for incubations of 30 minutes to 48 hours, at temperatures which can be between 4° C. and 40° C.

When the temperature or the time of incubation decreases, stimulation requires a higher concentration of mitogenic agent.

In practice, it is appropriate to carry out a stimulation with, for example, 0.1 to 10 μg/ml of PHA or 15 to 75 μg/ml of LPS for incubation times of 2 to 4 hours at a temperature of 20° to 37° C.

In particular, a direct stimulation of whole blood may be performed with, for example, 5 μg/ml of PHA and 25 μg/ml of LPS for incubations of 2 hours at 37° C.

Plasma concentration values of TNFα in both RIA and IRMA assay of the order of $10^3$ pg/ml, with significant variations from subject to subject, that is to say utilizable values which satisfy the conditions mentioned above, are thereby obtained.

This method of assaying monokines by direct stimulation of whole blood without resorting to a culturing stage has, in addition, a series of advantages which greatly facilitate their application in routine clinical practice, in that it is, in particular:

rapid (2 hours' incubation for the stimulation of whole blood, less than 2 hours' incubation for the assay in the case of IRMA immunoassay, like any plasma sample), simple, since it does not require conditions of sterility, or a culturing infrastructure, usable in places where blood samples are taken, equipped with a simple incubator, reliable, since reproducible from patient to patient and from sampling to sampling, since it eliminates all variations caused by culturing.

Furthermore, it is possible to provide, in assay kits, blood sampling tubes already containing the mitogenic agent, as will be enlarged upon later; otherwise, a time limit of two hours is available for beginning stimulation after drawing the sample. Accordingly, the incubator can be situated within a radius of two hours from the place where samples are taken.

Apart from phytohemagglutinin (PHA) or lipopolysaccharides (LPS), there may also be mentioned as a mitogenic agent, for example, phorbol myristate acetate, calcium ionophore, zymosan, digitonin, WGA (wheat germ agglutinin) or other lectins such as concanavalin.

As a guide, suitable concentration ranges for the use of these different mitogenic agents are indicated below.
1) TPA=MPA (phorbol myristate acetate) (MW=617) $10^{-7}$ to $10^{-9}$M
2) Calcium ionophore (MW=523) either the compound A 23187 (Sigma): 50 to 100 ng/ml, or ionomycin (Calbiochem): 0.5 to 2 μM.
3) Zymosan A: 300 μg/ml to 3 mg/ml.
4) Digitonin: 1 to 20 μg/ml.
5) WGA (wheat germ agglutinin): 10 to 100 μg/ml.
6) Con A (concanavalin A): 2 to 10 μg/ml.

Apart from EDTA, heparin or alternatively citrate may be mentioned as an anticoagulant according to the invention.

In a particular non-limiting embodiment of the assay according to the invention, these assays are immunoassays such as radioimmunoassay. In particular, they can be displacement immunoassays such as RIA assays, or two-site immunometric assays, in particular of the IRMA type.

Displacement assays are based on competition between the native antigen to be assayed and the labeled antigen for the antibody. After reaction, the antigen-antibody complex is separated from the free antigen. In general, measurement is performed on the bound antigen. Under these conditions and in the presence of a constant concentration of antibody, the measured signal decreases when the concentration of the antigen to be assayed increases.

In the case of two-site immunometric assays, the technique involves assaying an antigen with:

either two different and complementary antibodies which bind to two different epitopes, or two identical antibodies which bind to a repeating epitope.

The first antibody is immobilized on an insoluble phase (cellulose, plastic surface, Magnogel or the like), and the second, not adsorbed, bears a tracer or a label; it is referred to as labeled.

After reaction, separation of the free/bound complex is carried out by simple washing, and the bound complex is measured. Under these conditions, and in the presence of excess antibody, the measured signal increases when the concentration of the antigen to be assayed increases.

In these two types of assay, the tracer or label enables the immunological reaction to be quantified. The tracer or label is bound either to the antigen in the case of a displacement assay, or to the antibody for an immunometric assay. Irrespective of the type of assay, the choice of label depends both on the desired sensitivity and on the equipment in the analytical laboratories. At present, there are four main classes of tracers:

radioactive isotopes. Iodine-125 represents the best compromise between sensitivity and stability. The assays involving displacement are of the IRA (Radioimmunoassay) type, and the assays involving immunometry are of the IRMA (Immunoradiometric Assay) type;

enzymes, such as β-galactosidase, alkaline phosphatase or peroxidase. The assays involving displacement are of the ELISA (Enzyme-Linked Immunosorbent Assay) type, and the assays involving immunometry are of the IEMA (Immunoenzymometric Assay) type.

The subject of the present invention is also anti-TNFα antibodies and anti-IL-1β antibodies having high specificity, in particular not showing cross-reactions with respect to other cytokines, which are useful, in particular, for immunoassays of TNFα and of IL-1β, respectively.

More especially, there may be mentioned a rabbit anti-human TNFα polyclonal antibody or a rabbit anti-IL-1β polyclonal antibody and anti-TNFα monoclonal antibodies secreted by hybridomas produced by the fusion of mouse spleen cells and SP2-0 myeloma cells.

Finally, the subject of the present invention is also and naturally an assay kit or reagent kit for immunoassays of monokines, containing, among other reagents, a sample of a mitogenic agent such as PHA originating from a fully calibrated batch.

For example, the kit will contain a tube for sampling under vacuum, such as a vacutainer capable of withdrawing 5 to 10 ml of plasma, containing EDTA and PHA or only EDTA. In the latter case, the sample to be assayed, collected in the tube containing EDTA, will then be transferred to a tube containing PHA.

The provision of an assay kit containing the mitogenic agent contributes to the reliability of the assay, inasmuch as these mitogenic substances are complex lectins and hence difficult to reproduce from batch to batch, it being possible for variations in composition to give rise to differences in activity in stimulation.

According to another object of the present invention, the possibility was investigated of performing a direct plasma assay of monokines, in particular of TNFα, without even resorting to an activation of the whole blood with a mitogenic agent before separation of the blood cells, and, more generally, the possibility was investigated of directly assaying native TNF-α in biological fluids, that is to say not only plasma or serum, but also urine or peritoneal exudate, for example.

To this end, it was first sought to select a monoclonal antibody pair (adsorbed MAB/labeled MAB) which was the most sensitive in the context of carrying out an immunometric assay, especially of the IRMA type.

It emerges from the experiments illustrated in Example VI that a very sensitive monoclonal antibody pair, in particular for the assay of TNFα, does not, however, make it possible to retrieve, in an IRMA assay using this pair of monoclonal antibodies, the values for exogenous monokines added in a known quantity to biological fluids.

This phenomenon appears to be attributable to the presence of a binding protein in biological fluids, masking the epitopes for recognition of the monokine, in particular in the case of TNFα.

Nevertheless, it was discovered, according to the invention, that by employing, in the context of an immunometric assay, in particular an IRMA assay:

1) the action of a decomplexing or uncoupling agent, such as EDTA, by mixing, for example, this agent with the tracer (labeled and non-adsorbed antibody), and also 2) the use of a so-called "oligoclonal" system containing several monoclonal antibodies, containing, apart from the adsorbed MAB/labeled MAB pair selected on the basis of its sensitivity, at least one second adsorbed MAB selected to give the best possible recovery of known values for the monokine, in particular for TNFα in an immunometric assay, such as an IRMA assay using an adsorbed MAB/labeled MAB pair in which the adsorbed MAB is the said second adsorbed MAB. (lacuna)

The subject of the present invention is hence also an immunometric assay, such as an IRMA assay of a monokine, in particular of TNFα in a biological fluid, wherein at least two monoclonal antibodies recognizing different epitopes of the said monokine are used, the antibodies being adsorbed on a solid phase.

Suitably, a first adsorbed antibody is selected to give a very sensitive assay, in particular with a possible detection of a quantity as low as 10 pg/ml of monokine, a second adsorbed antibody being selected to give a maximum degree of recovery, in particular 100%, when known values for the said monokine (exogenous) are assayed.

Advantageously also, the assay is carried out in the presence of a decomplexing agent, such as EDTA, it being possible for the latter to be, for example, introduced with the tracer (labeled MAB).

The subject of the present invention is also an assay kit of the immunometric type for monokines, which contains at least two antibodies, recognizing different epitopes of the said monokine, adsorbed on a solid phase such as the inner wall of an assay tube or the surface of an assay bead.

Advantageously, this kit contains, among other reagents, a decomplexing agent such as EDTA.

Other characteristics and advantages of the present invention will become apparent in the light of the description which follows, given with reference to the following figures:

FIG. 1 shows the kinetics of release of TNFα (□), of IL-2 (Δ) and of γIFN (.) in cultures of mononuclear cells stimulated with PHA (1 μg/ml of γIFN and 10 μg/ml of IL-2 and TNF).

This figure establishes the rapidity of the secretion of TNFα into the stimulated culture media.

EXAMPLE I

Culturing of mononuclear cells

Figure 1:
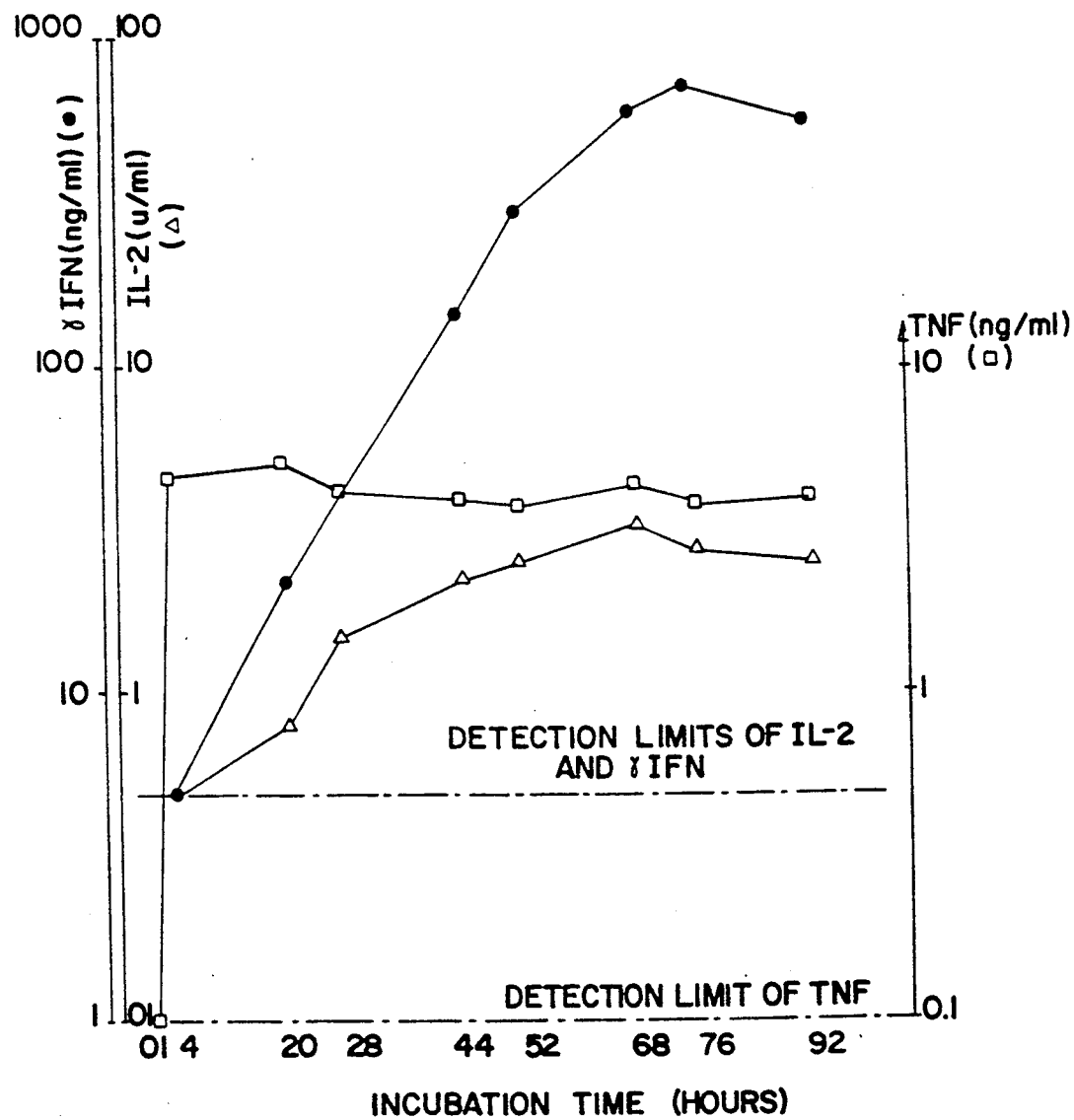

This culture method, generally used for studying the incorporation of tritiated thymidine (J. Exp. Med., 1979, 149, 1029), was, in fact, revised in respect of two parameters for application to the study of the release of TNFα: the culture time and the optimal doses of PHA.

The methodology of this type of culture is classical; however, two modifications were made thereto.

The first modification made to the classical cultures was the use of LeucoPrep ® (Becton Dickinson). This product permits simplified and faster separation of the mononuclear cells of peripheral blood, since it does not require treatment or prior dilution of the blood.

The second modification was: a DNA assay performed after culturing on the cell pellet. It is, in effect, useful to refer the levels of TNF detected by the RIA in the culture medium to the same number of cells, it being possible for the mitogen (PHA) used to show variable effects from one sample to another.

1. Isolation of the cells

The blood of a "normal" subject is withdrawn onto EDTA by Vacutainer tubes and deposited for 6 hours, where it is maintained at room temperature, in tubes containing the two phases of LeukoPrep (Becton Dickinson). These tubes are centrifuged at 900 g (20° C./15 min). Following this separation, the mononuclear cells form a visible white ring between the plasma and the organic phase. The cell layer is withdrawn under sterile conditions and deposited in a 50-ml conical-bottomed tube, in which the cells are washed twice consecutively with 30 ml of PBS buffer containing 0.1% NaN$_3$ (300 g/4° C./10 min and 400 g/4° C./10 min). The cells are taken up with 3 ml of RPMI 1640 culture medium containing glutamine, antibiotics and 5% of autologous serum. The cells are counted and the cell concentration is adjusted to $10^6$ cells/ml.

2. Culturing and stimulation with mitogen

Culturing is performed in 96-well NUNC plates, in which 200 μl of the cell suspension are deposited per well, to which suspension 22 μl of a phytohemagglutinin PHA (Wellcome) solution are added.

The cultures are incubated at 37° C. (5% CO$_2$ and 95% air).

The supernatants are withdrawn after centrifugation of the 96-well dishes (900 g/10 min/20° C.) and stored at −20° C. for radioimmunoassay. The cells—adhering to the bottom of the wells—are taken up with 200 μl of distilled H$_2$O and treated for two seconds with ultrasound. A 150 μl aliquot sample of cell content is assayed by the method of Paigen and Labarca to assess their DNA concentration.

All the results should be referred to the unit concentration of DNA.

3. Results

Two preliminary studies were carried out: a kinetic study and a dose-response study.

The final PHA concentrations studied for the dose-response effect vary from 0.02 to 50 µg/ml.

The kinetics were performed up to 4 days of incubation.

a. Dose-response effect of PHA γ-IFN shows bell-shaped response curves, with a maximum for doses of 1 and 2 µg/ml of PHA.

On the other hand, TNFα is not stimulated, relative to the control, by doses lower than 1 µg/ml; above this value, the progression is dose-dependent.

Finally, IL-2 shows a detectable stimulation only in a narrow concentration range—2 to 20 µg/ml—with a maximum at 5 µg/ml.

Conclusion: doses of 1 and of 10 µg/ml of PHA appear to be the most suitable for the three parameters γ-IFN, IL-2 and TNFα.

b. Kinetics

Stimulation of γ-IFN with 1 and 10 µg/ml shows similar kinetics, increasing up to 3 days of culture to reach a maximum in the hours which follow.

IL-2 is released in a different way according to the dose of PHA: with 1 µg/ml, there is a maximum at 28 h (between 20 and 44 h), followed by a decrease to attain, after 76 h, levels below the detection limit of the assay. With 10 µg/ml, in contrast, the release takes place gradually up to 52 h, after which it shows a plateau.

Figure 2:
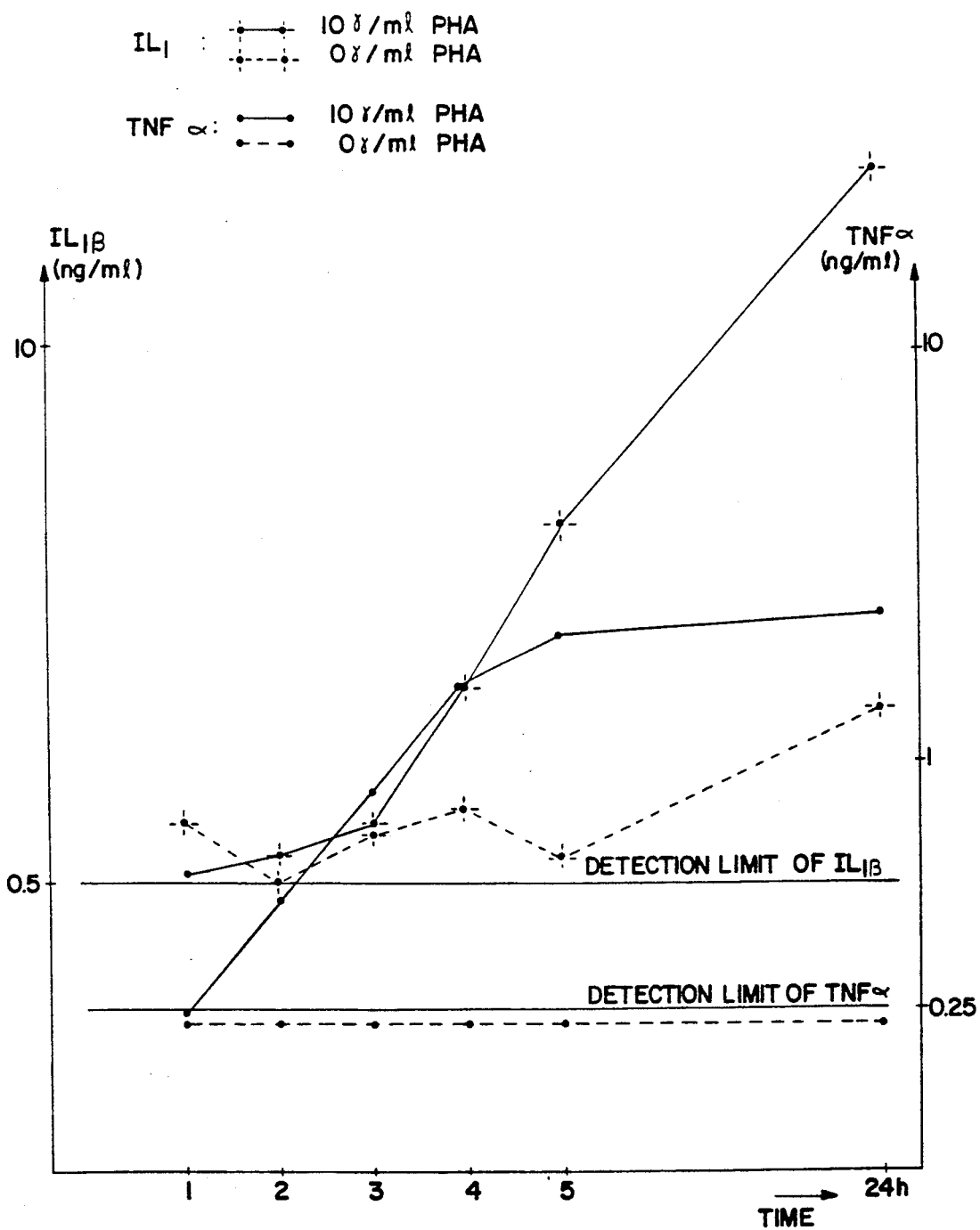
FIG. 2 shows the kinetics of release between 0 and 6 hours of TNFα and of IL-1β respectively, in cultures of mononuclear cells stimulated with PHA (10 μg/ml).

In contrast, TNFα and IL-1β are stimulated very early in the culture (less than 4 h) to levels which will be maintained subsequently and which are dose-dependent on the PHA, as is seen in FIG. 1 and FIG. 2.

4. Culturing for TNFα and IL-1β a. Culture time.

Kinetics of culture, stimulated, respectively, with 0, 1, 10 and 50 µg/ml of a batch of PHA (Wellcome), have enabled us to understand the principle governing release of TNFα and IL-1β with time in healthy subjects.

Results

For the 4 doses of PHA, the levels of TNFα and IL-1β in the culture medium increase up to 4 h of culture, but from this point, they remain constant up to more than 90 of culture for TNFα and continue to increase for IL-1β.

Conclusion

For the study of TNFα and of IL-1β, the cells in culture should be incubated for less than 4 hours with PHA; longer times not showing substantial modifications in the release of this molecule.

b. Doses of PHA to be used

A dose-response study was performed with variable doses of PHA (from 20 ng to 50 µg/ml) for 72 h of culture.

Results

Up to 500 ng/ml of PHA, modifications in the levels of TNFα are undetectable since below the detection limit of the assay. Above 500 ng/ml, in contrast, there is an almost linear dose-dependent relationship, this applying up to 50 µg/ml of PHA.

Conclusion

Large doses of PHA permit the maximum release of TNFα, whereas the other parameters (γ-IFN, IL-2) are decreased, probably as a consequence of a toxic effect of the PHA. In practice, doses of 1, 5 and 10 µg/m of the mitogen enable the potential of a cell for releasing its TNFα to be suitably assessed.

EXAMPLE II

Direct stimulation in the blood

On the basis of the relatively short times demonstrated above, a novel method was developed for short-circuiting the "culturing" part. Briefly, the donor's blood, withdrawn onto EDTA, is immediately brought into contact with PHA and incubated as it is. Following this operation, the blood is clarified by centrifugation. The TNFα is then assayed directly in the plasma obtained.

The blood of 9 "normal" subjects is withdrawn onto EDTA and immediately subjected to a stimulation with 0, 1 and 10 µg/ml of PHA. After, for example, 4 h of incubation at 37° C., the tubes are clarified and the plasmas assayed for TNFα.

As with the cultures of mononuclear cells, TNFα is also stimulated in a dose-dependent manner. Thus, compared with a mean for the controls (0 µg/ml of PHA) of 53.8±10.5 U/ml, 1 µg/ml gives average plasma levels of 512±273, and 10 µg/ml, 1966±804 pg/ml.

Choice of the conditions of temperature and of time of incubation

Direct stimulations with 5 µg/ml of PHA are formed on the blood of 4 "normal" subjects, for times of ½ h, 1 h, 2 h, 6 h and 22 h at 20° C. and at 37° C.

Results

1. At room temperature (20° C.), stimulations are always weaker than at 37° C.
2. For the 4 subjects, the largest plasma levels of TNFα are obtained after 2 h of incubation, and then remain stable at a plateau.

Conclusion

Direct stimulations with 5 µg/ml of PHA show the best results for incubations of 2 h at 37° C. The separation of the plasma after direct stimulation of the blood may be performed after a lapse of (lacuna) hours.

Importance of direct stimulation

This latter method possesses the substantial advantage of being, as has been seen.
1) fast (2 h) and
2) simple, since it does not require conditions of sterility or a culturing infrastructure.

It is hence usable in places where blood samples are taken, equipped with a simple incubator and a centrifuge, the sample then being sent to the assay laboratory, where the plasma will be separated as with any blood sample withdrawn from anticoagulant for routine plasma assay of a biological parameter.

EXAMPLE III

RIA type assay of TNFα

1. Immunization

Two rabbits received an intradermal injection of an emulsion of 0.5 ml of a saline solution containing 50 μg of TNFα (recombinant human TNFα) and 0.5 ml5 of FREUND's adjuvant according to the VAITUKAITIS method (6).

Four monthly booster injections were then administered using the same quantities of antigen. Blood samples were regularly collected from the marginal vein of the ear in each rabbit to test the titer of antiserum.

2. Labeling of TNFα

TNFα is labeled with iodine-125, using chloramine T according to the method of GREENWOOD (7). 5 μg of TNFα, dissolved in 5 μl of 0.05M phosphate buffer at pH 7.5, are incubated with 1 mCi of $^{125}I$, 5 μl of the same 0.5M buffer, pH 7.5, and 20 μg of chloramine T dissolved in 10 μl of 0.05M phosphate buffer, pH 7.5.

After 30 seconds, the reaction is stopped by adding 20 μg of metabisulfite diluted in 10 μl of the same buffer. After gel permeation chromatography with a Sephadex G-50 column (0.9×30 cm), the fractions corresponding to the first radioactive peak are passed through a Sephadex G-100 column (0.9×65 cm). The eluent for both columns is 0.05M phosphate buffer, pH 7.5, containing 0.05% of $NaN_3$ and 0.1% of bovine albumin.

3. Assay method and calibration curve

Incubations are performed at room temperature in 0.05M phosphate buffer, pH 7.5, containing 0.5% of BSA and 0.05% of $NaN_3$; 0.1 ml of buffer containing increasing quantities of unlabeled antigen (5, 10, 20, 50, 100, 200, 500 pg) or 0.1 ml of the sample to be assayed are mixed with 0.1 ml of antiserum at a dilution of 1/125,000; after preincubation overnight, 0.1 ml of incubation buffer containing the labeled antigen corresponding to approximately 30,000 cpm and rabbit serum at a dilution of 1% are added; incubation is carried out at room temperature for 20 to 24 hours. The antibody bound to the antigen is then precipitated by adding 1 ml of an incubation buffer containing 0.5% of Tween, 6% of polyethylene glycol, 0.2% of microcrystalline cellulose and 0.5% of anti-rabbit globulin serum prepared in sheep. After 20 minutes' incubation at room temperature, the antigen-antibody complex is sedimented by centrifugation for 20 minutes at 2,500 g. The supernatant is analyzed in a γ radioactivity counter.

Figure 3:
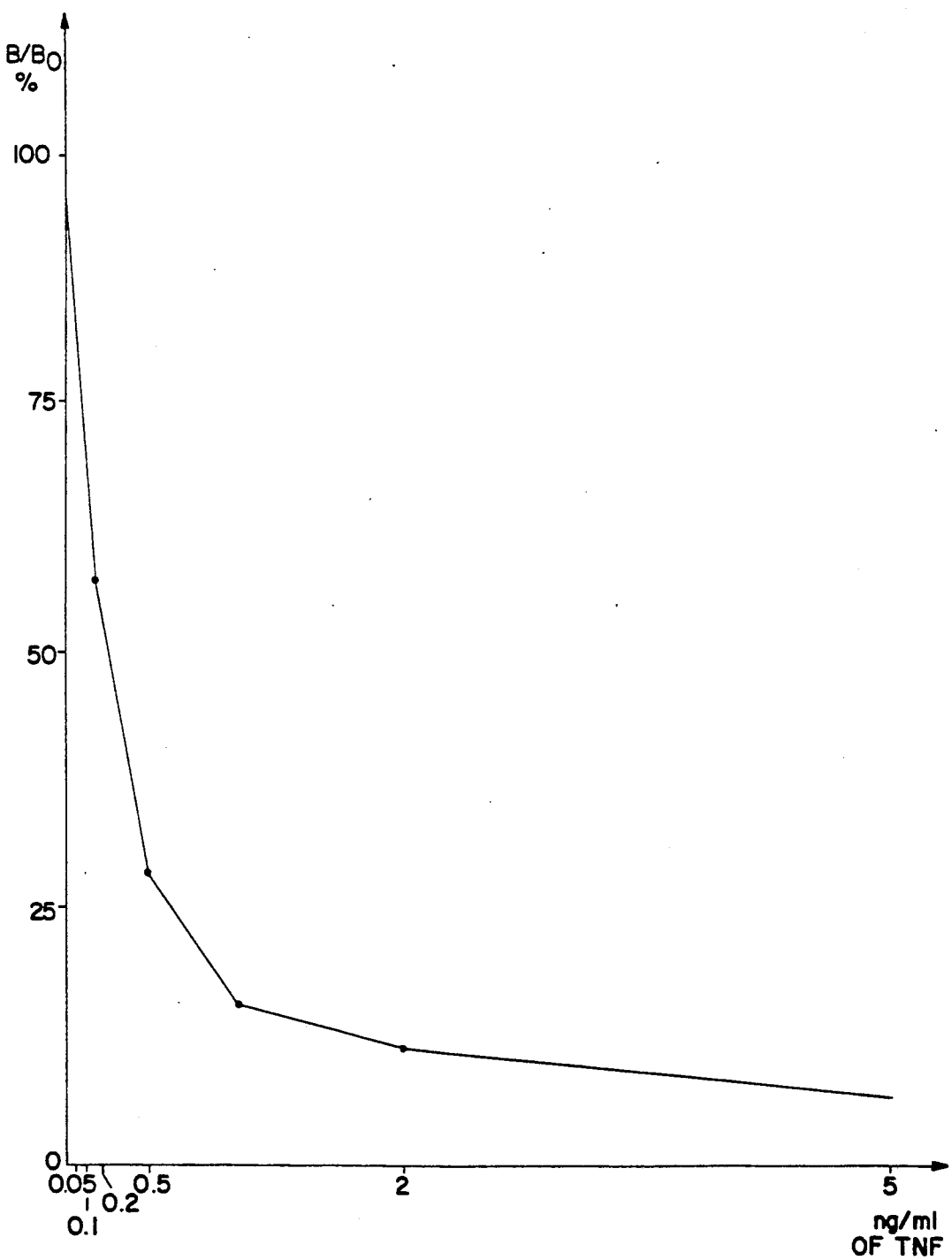
FIG. 3 shows an RIA calibration curve for TNFα.

FIG. 3 shows the RIA calibration curve obtained for a total incubation of two days at room temperature as follows:
antiserum + standard or sample: 1 day
+ TNF—$^{125}I$: 1 day
+ immunoprecipitant: 20 minutes
and after centrifugation and counting.

The radioactivity of the precipitate (the radioactivity of the labeled antigen bound to the antibody) is conventionally designated B. The total initial radioactivity, which is the same for all the tubes and is designated T, is also known. It is also possible to estimate the radioactivity of the free labeled antigen (designated Bo). It is generally sufficient to estimate $Bo = T - B$.

4. Specificity

Figure 5:
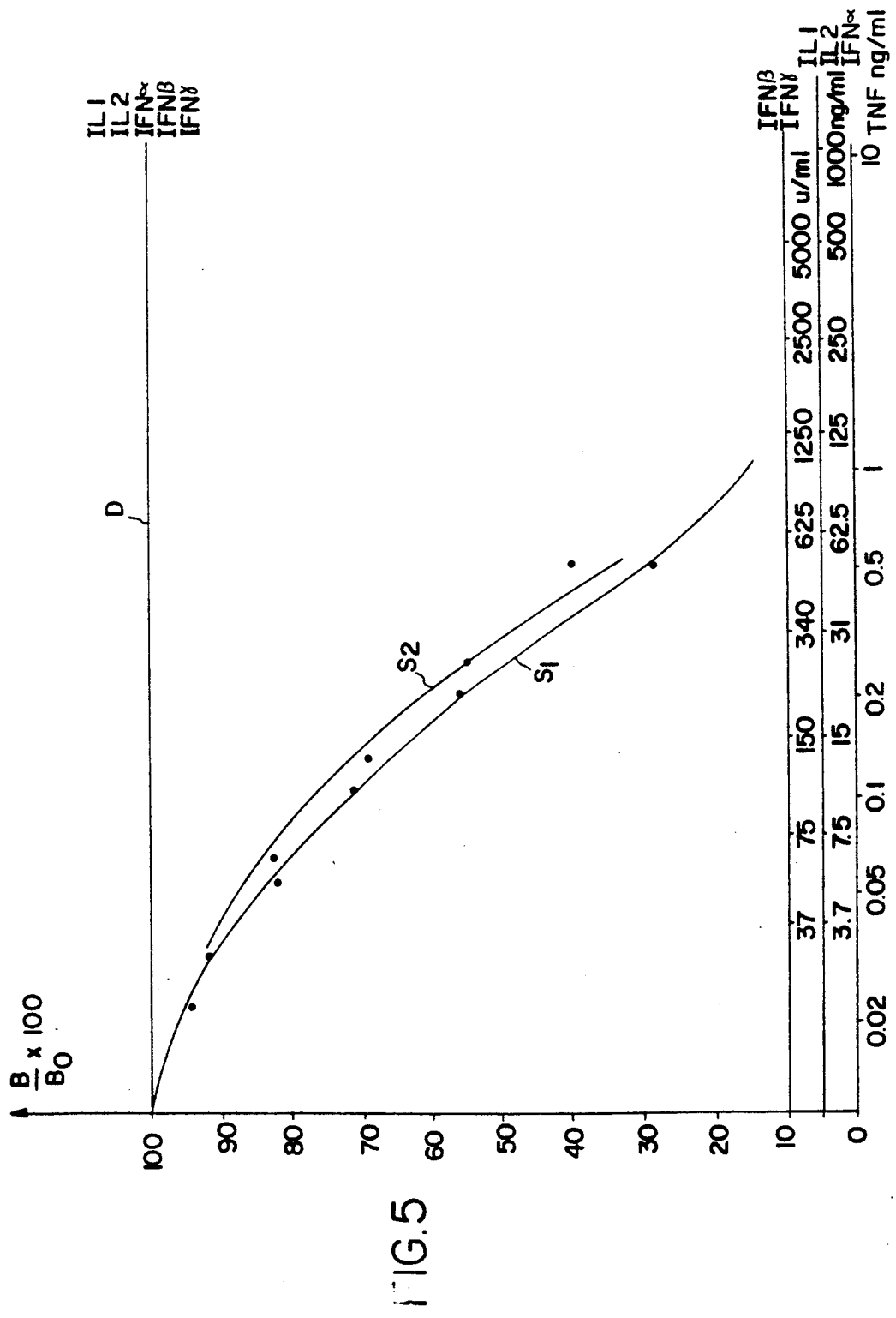
FIG. 5 shows the semilogarithmic specificity curve for the RIA assays of TNFα.

Recombinant β- and γ-IFN in concentrations of 0 to 5000 U/ml, and recombinant IL-1, IL-2 and γ-IFN in quantities of 1000 ng/ml were incapable of producing an inhibition of the binding of labeled TNFα to the antiserum, and hence in no way interfere in the assay of TNFα, as shown by the straight line D in FIG. 5.

Moreover, in this FIG. 5, the curve $S_1$ illustrates the displacement curve for cold standard TNF. The curve $S_2$ on the right illustrates the same curve for different dilutions of a culture medium possessing endogenous TNF.

The parallelism of these two curves confirms the identical immunological behavior between the standard and the culture medium, and hence confirms that it is possible to employ a stimulation.

EXAMPLE IV

IRMA type assay of TNFα-METHODS

1) Immunization

Two two-month old BALB/c strain female mice, originating from CEN-Mol, were immunized with recombinant TNF according to the following procedure:
a first intraperitoneal injection of 10 μg of TNF in 50% FREUND's complete adjuvant at day 0,
a second intraperitoneal injection of 10 μg of TNF in 50% incomplete FREUND's adjuvant on day 20,
a third intraperitoneal injection of 10 μg of TNF in PBS on day 50,
one of the two mice received a booster injection of 10 μg of TNFα in PBS intraperitoneally on day 75, and the second mouse after 4 months.

2) Fusion

The two mice were killed three days after the final booster. The spleens were removed and the spleen cells were prepared for fusion.

The cell fusion was performed according to the modified protocol of KOHLER (sic) and MILSTEIN (8). $9 \times 10^7$ spleen cells were fused with $1.6 \times 10^7$ SP2-O myeloma cells for the first mouse, and $4.8 \times 10^7$ spleen cells were fused with $10^7$ SP2-O myeloma cells for the second mouse, using polyethylene glycol 4000 as a fusion-inducing agent. After fusion, the cells were resuspended at a concentration of $2.5 \times 10^5$ cells/ml in a DMEM culture medium supplemented with 10% of horse serum, 10% of fetal calf serum, 4 μg/l of pig insulin, 2% of GIBCO solutions of penicillin/streptomycin, glutamine, nonessential amino acid, sodium pyruvate, hypoxanthine/thymidine and aminopterin. The solution was distributed into 20 96-well plates with 0.2 ml/well.

3) Screening of the hybridomas 10 days after the fusion, the culture medium of the plates was withdrawn and replaced by the same medium without aminopterin or insulin. The plates were screened with an inverted microscope to detect the wells with growing hybridomas. The presence of specific antibodies for TNF in the culture medium of the wells having positive hybridomas was selected as follows: 50 ml (sic) of the medium were withdrawn from the wells and incubated overnight with 40,000 cmp (sic) of TNF-$^{125}I$ in 0.2 ml of PBS buffer in hemolysis tubes. 0.1 ml of Wellcome donkey anti-mouse reagent coupled to cellulose were (sic) added into each tube for 15 minutes. 2 ml of water containing 0.1% of Tween 20 were added to the tubes before centrifugation at 4000 cpm (sic) for 10 minutes. The supernatant was withdrawn, and the radioactivity counted with a γ counter.

4) Production of monoclonal antibodies

The cells in the positive wells were transferred successively to 24-well plates and Petri dishes.

$5 \times 10^5$ cells per mouse were then injected intraperitoneally into BALB/c mice which had undergone an injection 10 days beforehand with 0.5 ml of pristane. 10 to 15 days later, the mice produced an ascitic fluid containing monoclonal antibodies. These ascitic fluids were collected and purified.

5) Purification of the monoclonal antibodies

The monoclonal antibodies in the ascitic fluid were purified through a Pharmacia protein A-sepharose affinity column.

6) Immunoradiometric assay

100 Nunc maxisorb tubes were coated using 200 μl of a solution containing 20 ng/ml of each monoclonal antibody. After 48 hours of coating, the antibody solution was removed and the tubes were saturated with phosphate buffer containing 0.5% of BSA for 4 hours. The tubes were then washed twice with 2 ml of water containing 0.1% of Tween 20. The tubes were dried by suction and stored in a sealed container with a drying agent.

25 μg of each monoclonal antibody were labeled with Na $^{125}$I by a chloramine T technique.

Each monoclonal antibody labeled with iodine-125 was used in an immunoradiometric assay with each of the monoclonal antibodies adsorbed on maxisorb tubes.

0.005 or 5 nanograms/ml of TNF standards in 0.1 ml of pH 7 phosphate buffer containing 0.5% of BSA were incubated with 200,000 cpm of $^{125}$I-labeled monoclonal antibodies in 50 microliters of pH 6 phosphate buffer, this being carried out for two hours in tubes coated with the different monoclonal antibodies. The mixture was then withdrawn and the tubes were washed twice with water containing 0.5% of Tween 20 and counted with a γ counter.

The pairs of monoclonal antibodies giving the best signal for the given TNFα concentrations were adopted for subsequent use.

EXAMPLE V

IRMA plasma assay of TNFα with activation

Results

1) Production of hybridomas

Spleen cells of Balb/c strain mice were fused with SP2-0 myeloma cells. 1380 supernatants of the wells containing at least one clone (hybridoma) were analyzed for the presence of antibodies recognizing TNFα.

19 hybridomas secreting anti-TNFα specific antibodies were selected. These hybridomas are as follows: 3C5, 1B5, 1D6, 3B5, 1B2, 4B3, 5C1, 2C4, 5A3, 2B3, 6A3, 4D1, 2A5, 3C3, 3E6, 3D3, 1F9, 2H7 and 10A2.

Table I below describes the characteristics of binding of iodine-125-labeled TNFα with the monoclonal antibodies secreted by 5 of these clones, namely 3D3, 1F9, 2H7, 3E6 and 10A2, which were the only ones which were initially available.

TABLE I

| Antibody | % of $^{125}$I-TNF binding (*) |
|---|---|
| 3D3 | 61 |
| 1F9 | 60 |
| 2H7 | 59 |
| 10A2 | 15 |
| 3E6 | 11 |

(*) binding of $^{125}$I-TNF by supernatant of 24-well plates.

2) Immunoradiometric assay

The culture of the five hybridomas was grown, and the cells were injected into Balb/c strain mice to obtain an ascitic fluid. The antibodies were purified from the ascitic fluid on a column of protein A. Purified antibodies were coated onto maxisorb tubes and labeled with Na$^{125}$I. All the combinations of each coated antibody with each labeled antibody were tested in an immunoradiometric assay with three standards.

The results appear in Table II below. The values given are in cpm of bound TNF-$^{125}$I.

TABLE II

| Labeled MAB | Standards ng/ml | Adsorbed MAB | | | |
|---|---|---|---|---|---|
| | | 3D3 | 1F9 | 2H7 | 10A2 |
| 3D3 | 0 | 366 | 379 | 438 | 479 |
| | 0.5 | 1055 | 1395 | 1728 | 1172 |
| | 5 | 4402 | 7855 | 10083 | 9935 |
| IF9 | 0 | 752 | — | — | 1276 |
| | 0.5 | 1330 | — | — | 1360 |
| | 5 | 6257 | — | — | 3894 |
| 2H7 | 0 | — | — | — | — |
| | 0.5 | — | — | — | — |
| | 5 | — | — | — | — |
| 10A2 | 0 | — | — | — | — |
| | 0.5 | — | — | — | — |
| | 5 | — | — | — | — |

Table II shows that the pair comprising adsorbed antibody 2H7 with labeled antibody 3D3 gives the best signal for each TNF concentration. These conclusions are confirmed by a second experiment performed with a wider range of standards, as shown in FIG. 3.

FIG. 3 (sic) shows IRMA standard curves with a total incubation of two hours at room temperature:

adsorbed antibody 1+standards or samples+iodine-125-labeled antibody 2 were incubated together for two hours.

Figure 4:
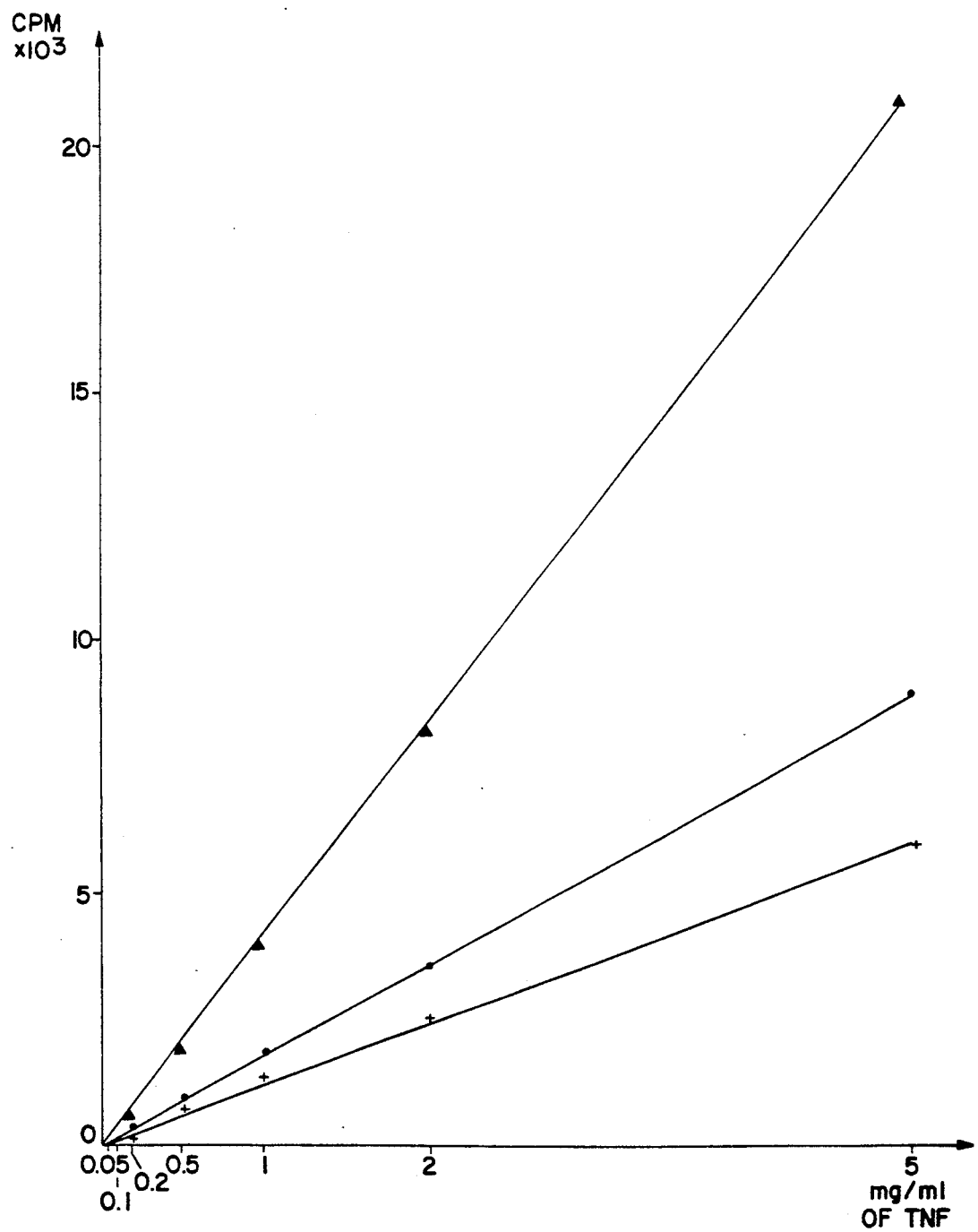
FIGS. 4 and 6 show IRMA standard curves for TNFα with various pairs of monoclonal antibodies (adsorbed MAB/labeled MAB).

Three curves were plotted in FIG. 4 respectively, for the pairs adsorbed 2H7/labeled 3D3 (▲), adsorbed 1F9/labeled 3D3 (●) and adsorbed 3D3/labeled 1F9 (+).

It emerges from Table II that the antibody 3D3 gives a significant response in coupling with itself in labeled form. This paradox may be explained by the fact that TNF can exist both in monomeric form and in di- or trimeric form. In the latter two cases, the same epitope may be available for the adsorbed antibody and the labeled antibody.

3) Specificity of the IRMA

The specificity of the assay was checked with six potential reagents capable of giving cross-reactions: TNFβ, interleukin-1, interleukin-2, interferon α, interferon γ and interferon β. The experiment was performed by replacing the TNFα standards by cross-reagent standards, concentrations being higher. These concentrations were

| | |
|---|---|
| TNFα | 0 to 50 ng/ml |
| TNFβ | 0 to 1000 ng/ml |
| IL-1 | 0 to 1000 ng/ml |
| IL-2 | 0 to 5000 U/ml |
| IFNα | 0 to 1000 ng/ml |
| IFNγ | 0 to 5000 U/ml |
| IFNβ | 0 to 5000 U/ml. |

None of these six reagents, potential as regards cross-reactions, gave rise to an interference affecting the titer of TNFα. Accordingly, the assay is completely specific for TNFα for the given concentrations of reagents. The proposed IRMA assay for TNFα is hence specific in respect of TNFβ, interleukin-1, interleukin-2, interferon α, interferon γ and interferon β.

4) Clinical assessment

The pair comprising adsorbed monoclonal antibodies 2H7 with labeled 3D3 was chosen for the following experiments.

The IRMA assay was compared with RIA in different series of clinical samples.

The first series consisted of supernatants of normal mononuclear cells, activated or otherwise with PHA. The comparison of the TNFα titers by RIA and IRMA for these samples is given in Table III below.

The second series consists of sera of normal donors after direct stimulation of the whole blood with 0.1 or 10 μg of PHA. The comparative results are given in Table IV.

In Table IV, the values are given in pg/ml of TNFα.

A denotes the experiment without stimulation by PHA,

B denotes the experiment with stimulation by 1 μg/ml of PHA,

C denotes the experiment with stimulation by 10 μg/ml of PHA.

All the IRMA procedures were performed in two hours at room temperature in one stage.

TABLE III

| Supernatant | Polyclonal RIA TNFα values (ng/ml) | Monoclonal IRMA TNFα values (ng/ml) |
|---|---|---|
| 1 | 1.2 | 1.2 |
| 2 | 0.55 | 0.51 |
| 3 | 0.86 | 1.00 |
| 4 | 0.34 | — |
| 5 | 0.52 | 0.65 |
| 6 | 2.8 | 3.1 |
| 7 | 0.48 | 0.87 |
| 8 | 0.51 | 0.56 |
| 9 | 0.80 | 0.36 |
| 10 | 1.00 | 0.95 |

TABLE IV

| Sample | Polyclonal RIA TNFα values (pg/ml) | Monoclonal IRMA TNFα values (pg/ml) |
|---|---|---|
| 1-A | 70 | — |
| 1-B | 780 | 760 |
| 1-C | 3000 | 2440 |
| 2-A | 48 | — |
| 2-B | 1050 | 220 |
| 2-C | 2800 | 2000 |
| 3-A | 68 | — |
| 3-B | 194 | — |
| 3-C | 950 | 660 |
| 4-A | 36 | — |
| 4-B | 240 | — |
| 4-C | 1090 | 250 |
| 5-A | 52 | — |
| 5-B | 360 | 150 |
| 5-C | 830 | 650 |
| 6-A | 50 | — |
| 6-B | 520 | — |
| 6-C | 1720 | 1400 |
| 7-A | 50 | — |
| 7-B | 545 | 400 |
| 7-C | 2550 | 2000 |
| 8-A | 52 | — |
| 8-B | 460 | 240 |

Table V below shows comparative RIA and IRMA results for a third series of 20 assays of sera of healthy subjects without stimulation. (This TNFα by IRMA assay was not detectable with the pair 2H7/3D3).

Table VI shows a series of 20 assays of sera of subjects suffering from pancreatitis without stimulation.

TABLE V

| Serum | RIA TNFα (pg/ml) | IRMA TNFα (pg/ml) |
|---|---|---|
| 1 | 42 | — |
| 2 | 44 | — |
| 3 | 53 | — |
| 4 | 62 | — |
| 5 | 23 | — |
| 6 | 31 | — |
| 7 | 39 | — |
| 8 | 77 | — |
| 9 | 58 | — |
| 10 | 36 | — |
| 11 | 34 | — |
| 12 | 45 | — |
| 13 | 74 | — |
| 14 | 59 | — |
| 15 | 29 | — |
| 16 | 28 | — |
| 17 | 47 | — |
| 18 | 47 | — |
| 19 | 69 | — |
| 20 | 51 | — |

TABLE VI

| Serum | RIA TNFα (pg/ml) | IRMA TNFα (pg/ml) |
|---|---|---|
| 1 | 183 | — |
| 2 | 142 | — |
| 3 | 56 | — |
| 4 | 184 | — |
| 5 | 145 | — |
| 6 | 165 | — |
| 7 | 179 | — |
| 8 | 196 | — |
| 9 | 105 | — |
| 10 | 157 | — |
| 11 | 162 | — |
| 12 | 197 | — |
| 13 | 134 | — |
| 14 | 141 | — |
| 15 | 167 | — |
| 16 | 109 | — |
| 17 | 125 | — |
| 18 | 112 | — |
| 19 | 115 | — |
| 20 | 134 | — |

In conclusion, the titration of serum TNFα in blood samples activated with PHA or in supernatants of monocytes activated with PHA give large values which are satisfactory in RIA and IRMA from the standpoint of the sensitivity of these assay. In contrast, in the absence of stimulation, a leveling of the values is observed, the latter being, furthermore, too low relative to the detection limit of the assays.

EXAMPLE VI

IRMA assay of TNFα in biological fluids without activation

Supplementary antibodies were obtained on performing a second fusion.

The 19 pairs of anti-TNF monoclonal antibodies obtained were tested in respect of their sensitivity in the context of an IRMA assay.

The results are expressed in Table VII below in the following manner:

An index from 0 to 11 was assigned to each pair of antibodies. This index represents the capacity of two monoclonal antibodies to give a signal in the presence of TNFα.

Each I-125-labeled monoclonal antibody is tested with each adsorbed monoclonal antibody as follows: TNFα standards of 0.500 and 5000 pg/ml are incubated with an I-125-labeled MAB emitting 200,000 cpm in a tube coated with monoclonal antibodies for two hours. After washing, the tubes are counted in a gamma counter and, for each pair of MAB, an index is assigned, established as follows:

Index 0: pair giving less than 500 cpm between 0 and 500 pg of TNFα/ml and less than 5000 cpm between 0 and 5000 pg of TNFα/ml.

Index 1: pair giving more than 500 and less than 1000 cpm between 0 and 500 pg/ml of TNFα and more than 5000 and less than 10,000 cpm between 0 and 5000 pg of TNFα/ml.

Index 2: pair giving more than 1000 and less than 2000 cpm between 0 and 500 pg of TNFα/ml and more than 10,000 and less than 20,000 cmp (sic) between 0 and 5000 pg of TNFα/ml.

Index 3: pair giving more than 2000 and less than 3000 cpm between 0 and 500 pg of TNFα/ml and more than 20,000 and less than 30,000 cpm between 0 and 5000 pg of TNFα/ml.

Index 4: pair giving more than 3000 and less than 4000 cpm between 0 and 500 pg of TNFα/ml and more than 30,000 and less than 40,000 cpm between 0 and 5000 pg of TNFα/ml.

Index 5: pair giving more than 4000 and less than 5000 cpm between 0 and 500 pg of TNFα/ml and more than 40,000 and less than 50,000 cpm between 0 and 5000 pg of TNFα/ml.

Index 7: pair giving more than 6000 and less than 7000 cpm between 0 and 500 pg of TNFα/ml of (sic) more than 60,000 and less than 70,000 cpm between 0 and 5000 pg of TNFα/ml.

Index 11: pair giving more than 10,000 and less than 11,000 cpm between 0 and 500 pg of TNFα/ml and more than 100,000 and less than 110,000 cpm between 0 and 5000 pg of TNFα/ml.

TABLE VII

| | SELECTION OF PAIRS OF MAB FOR IRMA Labeled MAB | | | | | | | | | | | | | | | | | |
|---|---|---|---|---|---|---|---|---|---|---|---|---|---|---|---|---|---|---|
| adsorbed MAB | 3D3 | 1F9 | 2H7 | 10A2 | 3C5 | 1B5 | 1D6 | 3B5 | 1B2 | 4B3 | 5C1 | 2C4 | 5A3 | 2B3 | 6A3 | 4D1 | 2A5 | 3C3 |
| 3D3 | 0 | 2 | 0 | 0 | 1 | 2 | 0 | 0 | 0 | 1 | 2 | 0 | 0 | 0 | 0 | 0 | 0 | 0 |
| 1F9 | 1 | 0 | 0 | 0 | 0 | 0 | 1 | 0 | 0 | 0 | 0 | 0 | 0 | 0 | 0 | 0 | 0 | 0 |
| 2H7 | 4 | 2 | 2 | 0 | 1 | 2 | 2 | 2 | 1 | 0 | 2 | 1 | 1 | 0 | 1 | 1 | 0 | 2 |
| 10A2 | 2 | 0 | 0 | 0 | 0 | 2 | 0 | 1 | 0 | 0 | 2 | 0 | 0 | 0 | 0 | 0 | 2 | 1 |
| 3C5 | 4 | 0 | 0 | 0 | 1 | 3 | 3 | 4 | 3 | 1 | 2 | 0 | 0 | 0 | 3 | 0 | 2 | 3 |
| 1B5 | 5 | 2 | 0 | 0 | 3 | 0 | 1 | 1 | 0 | 0 | 0 | 0 | 3 | 0 | 1 | 0 | 0 | 1 |
| 1D6 | 0 | 2 | 0 | 0 | 3 | 0 | 0 | 1 | 0 | 0 | 1 | 0 | 0 | 0 | 0 | 0 | 0 | 0 |
| 3B5 | 0 | 2 | 0 | 0 | 3 | 0 | 0 | 0 | 0 | 0 | 0 | 0 | 0 | 0 | 0 | 0 | 0 | 0 |
| 1B2 | 0 | 0 | 0 | 0 | 7 | 0 | 0 | 0 | 0 | 0 | 0 | 0 | 0 | 0 | 0 | 0 | 8 | 0 |
| 4B3 | 5 | 0 | 0 | 0 | 3 | 0 | 0 | 2 | 0 | 0 | 0 | 0 | 2 | 0 | 0 | 0 | 0 | 0 |
| 5C1 | 4 | 1 | 0 | 0 | 3 | 0 | 1 | 1 | 0 | 0 | 0 | 1 | 2 | 0 | 1 | 0 | 0 | 1 |
| 2C4 | 2 | 0 | 0 | 0 | 0 | 2 | 0 | 0 | 0 | 0 | 2 | 0 | 5 | 0 | 0 | 0 | 2 | 0 |
| 5A3 | 1 | 2 | 0 | 0 | 0 | 2 | 0 | 0 | 0 | 1 | 2 | 1 | 0 | 0 | 0 | 0 | 0 | 0 |
| 2B3 | 0 | 0 | 2 | 0 | 11 | 0 | 1 | 0 | 0 | 0 | 0 | 0 | 0 | 0 | 0 | 0 | 0 | 0 |
| 6A3 | 0 | 2 | 0 | 0 | 5 | 2 | 0 | 0 | 0 | 2 | 0 | 0 | 0 | 0 | 0 | 0 | 0 | 0 |
| 4D1 | 2 | 3 | 0 | 0 | 0 | 2 | 1 | 0 | 0 | 0 | 1 | 1 | 0 | 0 | 0 | 0 | 2 | 0 |
| 2A5 | 0 | 2 | 2 | 0 | 5 | 0 | 0 | 0 | 0 | 0 | 0 | 0 | 0 | 0 | 0 | 0 | 0 | 2 |
| 3C3 | 1 | 2 | 0 | 0 | 2 | 0 | 0 | 0 | 0 | 0 | 0 | 0 | 0 | 0 | 0 | 0 | 2 | 0 |

Figure 6:
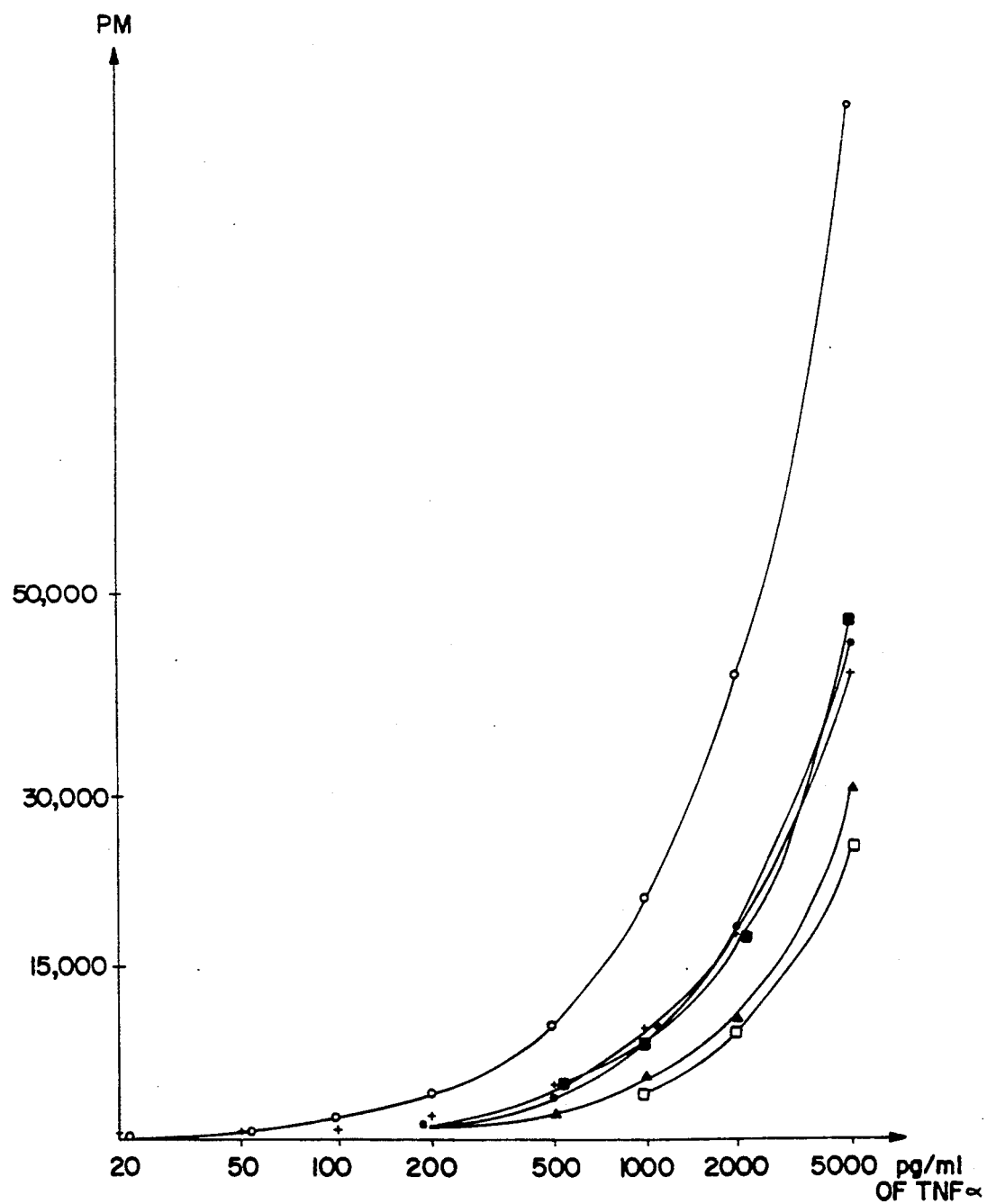

From Table VII, 7 pairs with an index greater than 5 were selected for more extensive investigations. 6 of these pairs were tested with a wider range of standards, as shown in FIG. 6. FIG. 6 shows IRMA standard curves obtained with the six pairs of antibodies after a total incubation of 24 hours at room temperature:
adsorbed antibody 1+standard or sample+Na$^{125}$I-labeled antibody 2 incubated together for 24 hours.

The data in Table VIII below are reproduced in FIG. 6.

It emerges from this FIG. 6 that the most sensitive pair of antibodies is the pair adsorbed 2B3+labeled 3C5.

TABLE VIII

| TNFα | ▲ 1B5/3D3 | ● 4B3/3D3 | + 1B2/3C5 | ○ 2B3/2C5 | □ 6A3/3C5 | ■ 2A5/3C5 |
|---|---|---|---|---|---|---|
| Total | 197361 | 196830 | 205858 | 205624 | 204785 | 284368 |
| 0 pg/ml | 756 | 909 | 524 | 720 | 656 | 1202 |
| 20 pg/ml | 715 | 845 | 1218 | 1137 | 1177 | 1859 |

TABLE VIII-continued

| TNFα | ▲ 1B5/3D3 | ● 4B3/3D3 | + 1B2/3C5 | ○ 2B3/2C5 | □ 6A3/3C5 | ■ 2A5/3C5 |
|---|---|---|---|---|---|---|
| 50 pg/ml | 898 | 1242 | 1432 | 1562 | 903 | 1865 |
| 100 pg/ml | 1073 | 1221 | 1761 | 2686 | 1454 | 2033 |
| 200 pg/ml | 1868 | 2171 | 4575 | 4805 | 1760 | 2792 |
| 500 pg/ml | 3054 | 4820 | 5747 | 11007 | 2954 | 6098 |
| 1000 pg/ml | 6535 | 9329 | 10377 | 11016 | 5223 | 10344 |
| 2000 pg/ml | 11807 | 19712 | 18930 | 42136 | 10302 | 19414 |
| 5000 pg/ml | 32234 | 45508 | 42286 | 33876 | 26319 | 47771 |

From this point, the investigation proceeded in two stages:
1st stage: development of a sensitive IRMA for the assay of TNFα in culture medium with the pair of antibodies 2B3/3C5.
2nd stage: extension to the IRMA assay of native TNFα present in biological fluids. This extension necessitated the use of uncoupling agents and the addition of supplementary adsorbed MAB on the solid phase ("oligoclonal" mixtures).

1) Development of an IRMA for the Assay of TNFα in Culture Medium 1.1 Pair of MAB used: adsorbed 2B3+Na$^{125}$I-labeled 3C5.
1.2 Sensitivity: The 2B3/3C5 standard curve of FIG. 6 shows a sensitivity of the order of 10 pg/ml of TNFα.
1.3 Specificity: The specificity of the pair 2B3/3C5 was tested for six reagents capable of giving cross-reactions:
TNFα (up to 1000 ng/ml)
IL-1β (up to 1000 ng/ml)
IL-2 (up to 500 units/ml)
IFNα (up to 100 ng/ml)
IFNγ (up to 5000 units/ml) and
IFNβ (up to 5000 units/ml).
None of these six cross-reagents interfere with the assay of TNFα.
1.4 Test of recovery: The recovery of human recombinant TNF (hr-TNFα) to be added to the culture medium is greater than 90%.
1.5 Dilution test: The dilution of a TNFα-rich culture medium in culture medium is shown in Table IX. The results in Table IX show a 90% recovery for dilutions ranging up to 1/16.

TABLE IX

| Dilution test in culture medium | | | |
|---|---|---|---|
| Dilution | Calculated values (pg/ml) | Measured values | % |
| 1/1 | | 4039 | |
| 1/2 | 2020 | 1826 | 90 |
| 1/4 | 1010 | 903 | 89 |
| 1/8 | 505 | 443 | 88 |
| 1/16 | 253 | 224 | 89 |

1.6 Correlation with RIA

Figure 7:
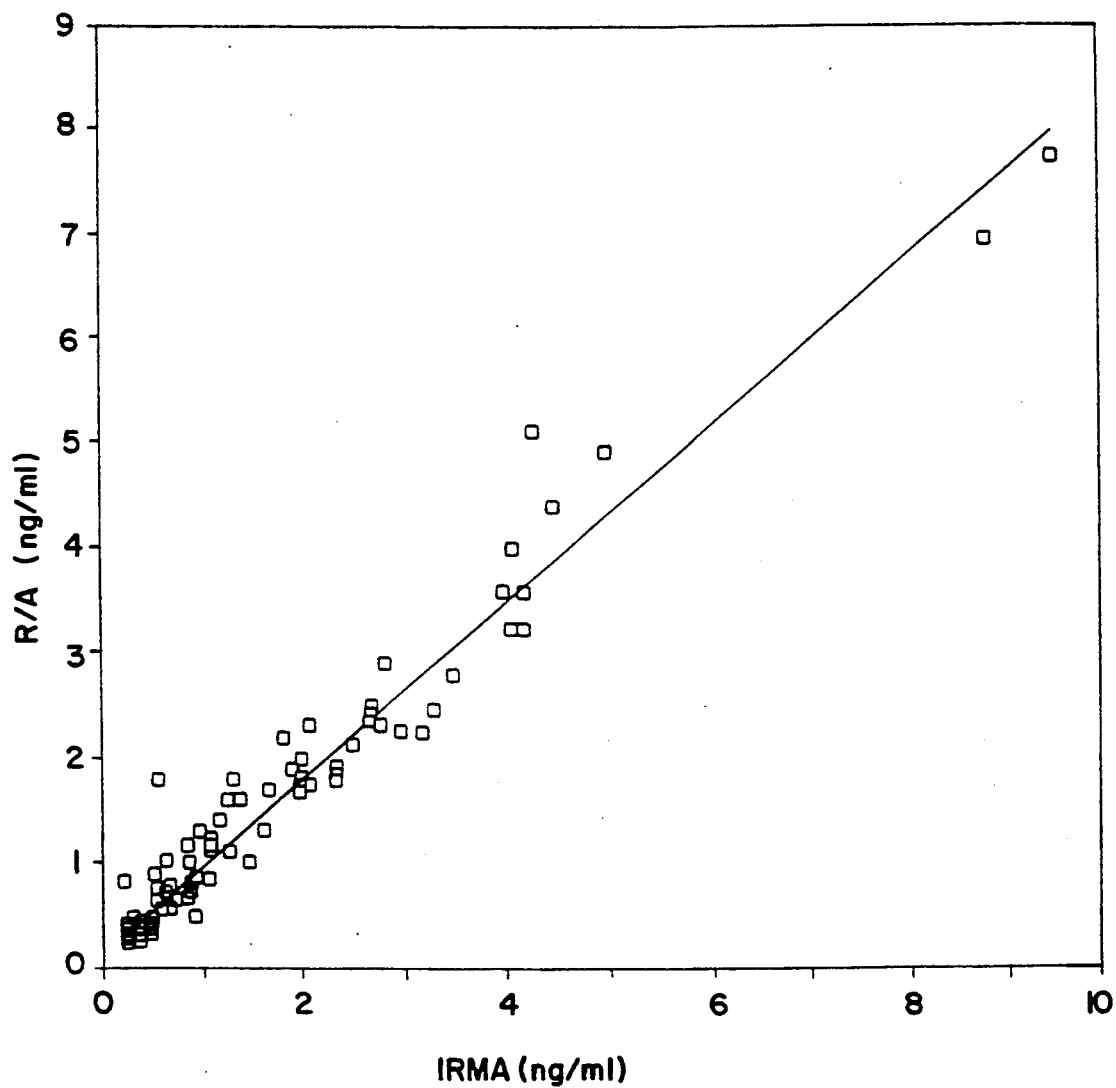
FIG. 7 shows a curve of correlation between IRMA and RIA assays of TNFα.

A correlation was established between values for clinical samples assayed by RIA or by 2B3/3C5 IRMA. These samples consist of 109 culture supernatants of PBL originating from 22 different subjects and activated with 0, 0.2, 1, 5 or 10 μg/ml of PHA.
The samples were chosen as follows: 11 normal; 4 cancer of the larynx; 4 diabetic; and 3 rheumatoid polyarthritis. The correlation between RIA and IRMA is given in FIG. 7. The correlation coefficient is 0.97, which shows a good agreement between the two tests.

2. Assay of TNFα in Biological Fluids by IRMA

2B3/3C5 IRMA shows excellent results for the assay of TNFα in culture supernatants. It was desired to extend this assay to TNFα present in biological fluids of certain patients (subjects with septic shock or graft rejection).

2.1 Test of recovery in serum

A known quantity of hr-TNFα was added to sera of normal subjects or of subjects having septic shock, and the TNFα in these sera was then titrated with 2B3/3C5 IRMA. The results are as follows:
recovery in normal serum: 40 to 50%
recovery in serum of subject with shock: 10 to 20%.
These poor recovery tests suggest the presence in the sera of a substance, such as protein binding TNFα, which interferes with the IRMA assay and which is present to a greater extent in the sera of subjects with septic shock.

2.2 Test of different treatments to remove the serum interference

It was endeavored to abolish the interference with the IRMA assay of TNF in the serum by adding uncoupling agents or by inactivating treatments. These different attempts are recorded in Table X.
Table X shows the action of the different treatments on the sensitivity of the 2B3/3C5 IRMA curve (standard points 0, 100 and 5000), as well as their effects on the recovery of hr-TNFα added to a serum of a subject with septic shock. Treatments which affect the sensitivity of the test have been rejected (for example 500 mM DTT), as well as those which, while improving the recovery, involve an additional stage (preheating of the samples to 56° C. or precipitation with PEG).
The addition of EDTA, which permits a recovery of 96% instead of 19%, was adopted.

TABLE X

TEST OF DIFFERENT TREATMENTS ON THE SERUM INTERFERENCE

TREATMENT;  A/NOTHING
B/DTT 50 mM 37° C. 10'    (DTT = Dithiothreitol)
C/EDTA 10 mM
D/EDTA 10 mM + CAC12 20 mM
E/NASCN 10 mM
F/NASCN 300 mM

TABLE X-continued
TEST OF DIFFERENT TREATMENTS ON THE SERUM INTERFERENCE

G/PEG 9% AND CENTRIFUGATION
H/PEG 12.2% AND CENTRIFUGATION
I/PEG 15% AND CENTRIFUGATION
J/56° C.
K/65° C.
L/PH3
M/PH13
N/CON A 100 G/ml
O/CON A 500 G/ml
P/CON A 1000 G/ml
Q/PB. 100 L          (PB = Phosphate buffer)
R/PB. 200 L
Total count = 193000

| TNF values γ (pg/ml) | A | B | C | D | E | F | G | H | I |
|---|---|---|---|---|---|---|---|---|---|
| STD. 0 (*) | 665.0 | 1,480.0 | 634.5 | 940.0 | 821.5 | 749.5 | 724.0 | 902.5 | 781.0 |
| STD 100 | 2,598.5 | 1,602.5 | 3,025.5 | 2,760.0 | 2,031.5 | 1,738.0 | 2,745.5 | 2,701.5 | 2,894.0 |
| STD 5000 | 84,483.0 | 4,819.0 | 89,645.5 | 93,958.5 | 67,547.0 | 57,368.0 | 94,958.5 | 87,768.0 | 89,746.0 |
| shock + 5000 | 15,870.5 | 6,945.0 | 85,938.0 | 28,272.0 | 34,881.0 | 45,871.0 | 81,273.5 | 87,385.5 | 90,354.0 |
| % recovery | 18.8 | 144.1 | 95.9 | 30.1 | 51.6 | 80.0 | 85.6 | 99.6 | 100.7 |

| TNF values γ (pg/ml) | J | K | L | M | N | O | P | Q | R |
|---|---|---|---|---|---|---|---|---|---|
| STD. 0 | 416.5 | 558.5 | 514.0 | 420.5 | 622.5 | 632.0 | 668.0 | 751.0 | 984.5 |
| STD 100 | 2,016.0 | 2,349.5 | 2,013.5 | 1,112.0 | 2,392.5 | 2,616.0 | 2,474.0 | 2,161.5 | 2,336.0 |
| STD 5000 | 76,684.0 | 80,743.5 | 6,439.5 | 2,376.0 | 84,458.5 | 75,287.5 | 75,961.5 | 77,740.0 | 72,251.5 |
| shock + 5000 | 83,593.5 | 75,649.0 | 2,029.5 | 1,922.5 | 13,036.5 | 12,214.5 | 18,310.5 | 10,286.5 | 9,970.5 |
| % recovery | 109.0 | 93.7 | 31.5 | 80.9 | 15.4 | 16.2 | 24.1 | 13.2 | 13.8 |

(* STD — standard)

The effect of EDTA was confirmed on a larger number of samples; see Table XI below.

Generally speaking, EDTA permits an average recovery of 80% instead of 50% in the sera of subjects with septic shock or in the sera of normal subjects.

This is a significant but inadequate improvement.

TABLE XI
Degree of recovery in different biological samples with and without EDTA

| Sample | EDTA 0% | EDTA 10% |
|---|---|---|
| Normal plasma | 60% | 86% |
| Normal serum 1 | 38% | 83% |
| Normal serum 2 | 30% | 88% |
| Shock 1 | 6% | 72% |
| Shock 2 | 17% | 51% |

2.3 Test of other pairs of antibodies

It was investigated whether the serum interference with the 2B3/3C5 IRMA pair was also found for other pairs of antibodies of FIG. 6.

Table XII shows the recovery of 5000 pg/ml of hr-TNF in 3 sera of subjects with septic shock and 2 normal sera with the following IRMA: 1B5/3D3; 4B3/3D3; 1B2/3C5; and 6A3/3C5. It may be stated on the basis of observation of these results that the interfering serum substance does not act with all the pairs. Interference is greatest for the pair 2A5/3C5, equivalent for the pairs 2B3/3C5 and 4B3/3D3, and a little less pronounced for the pair 1B2/3C5.

In contrast, the pairs 1B5/3D3 and 6A3/3C5 have a recovery of more than 100%.

The fact that the pair 6A3/3C5 uses the same tracer as 2B3/3C5 and behaves differently from the standpoint of recovery suggests that the interference is not linked with the tracer.

It is hence the case that the adsorbed antibodies recognize different epitopes, either more or less close to the binding site of the interfering substance (antibodies 2B3, 4B3, 2A5 and 1B2), or remote from this site (antibodies 6A3 and 1B5).

Since the pairs 1B5/3D3 and 6A3/3C5 were not sufficiently sensitive to be used as they were, the possibility was envisaged of adsorbing jointly on the solid phase the antibodies 1B5 and 2B3 on the one hand, or the antibodies 6A3 and 2B3 on the other hand, in order to combine their respective advantages (good recovery in the case of 1B5 and 6A3 and good sensitivity in the case of 2B3).

TABLE XII
STUDY OF THE SERUM INTERFERENCE WITH OTHER IRMA PAIRS

| Pair | 1B5/3D3 | 4B3/3D3 | 1B2/3C5 | 2B3/3C5 | 6A3/3C5 | 2A5/3C5 |
|---|---|---|---|---|---|---|
| Total counts | 197361 | 196830 | 205050 | 205624 | 204705 | 204360 |
| TNF standard curves | | | | | | |
| 0 pg/ml | 756 | 909 | 524 | 780 | 656 | 1202 |
| 20 pg/ml | 715 | 845 | 1218 | 1137 | 1177 | 1059 |
| 50 pg/ml | 898 | 1242 | 1432 | 1562 | 903 | 1065 |
| 100 pg/ml | 1073 | 1221 | 1761 | 2686 | 1454 | 2039 |
| 200 pg/ml | 1860 | 2171 | 2575 | 4805 | 1760 | 2792 |
| 500 pg/ml | 3054 | 4820 | 5747 | 11007 | 2964 | 6090 |
| 1000 pg/ml | 6535 | 9329 | 10377 | 22016 | 5228 | 10844 |
| 2000 pg/ml | 11807 | 19712 | 18930 | 42136 | 10302 | 19414 |
| 5000 pg/ml | 32234 | 45500 | 42286 | 93876 | 26819 | 47771 |
| septic shock (H8) + 5000 pg/ml | 7731 | 1156 | 2716 | 719 | 9625 | 203 |
| septic shock (T1) + 5000 pg/ml | 5113 | 1314 | 3250 | 1137 | 4398 | 168 |

TABLE XII-continued

STUDY OF THE SERUM INTERFERENCE WITH OTHER IRMA PAIRS

| | | | | | | |
|---|---|---|---|---|---|---|
| septic shock (O1) + 5000 pg/ml | 6746 | 1367 | 2169 | 834 | 6674 | 325 |
| normal human serum + 5000 pg/ml | 7417 | 2226 | 4094 | 1677 | 9532 | 1061 |
| normal human serum + 5000 pg/ml | 7911 | 2516 | 4793 | 1787 | 6850 | 1086 |
| buffer + 5000 pg/ml | 4582 | 5041 | 5042 | 4669 | 5049 | 4760 |
| % recovery | 168,7 | 22,9 | 53,9 | 15,4 | 190,6 | 4,3 |
| % | 111,6 | 26,1 | 64,5 | 24,4 | 87,1 | 3,5 |
| % | 147,2 | 27,1 | 43,0 | 17,9 | 132,2 | 6,8 |
| % | 161,9 | 44,2 | 81,2 | 35,9 | 188,8 | 22,3 |
| % | 172,7 | 49,9 | 95,1 | 38,3 | 135,7 | 22,8 |
| % | 100 | 100 | 100 | 100 | 100 | 100 |

2.4 IRMA with an oligoclonal solid phase

Table XIII shows the test of recovery with the oligoclonal pairs 1B5+2B3/3C5 and 6A3+2B3/3C5, in comparison with 2B3/3C5 alone. The tests are carried out in the presence of EDTA. It was observed that the two oligoclonal IRMA have a recovery of more than 100% in the sera of subjects with septic shock or in the sera of normal subjects, while the reference pair at (sic) a recovery of less than 100% in the normals and more than 80% in the shock sera. Moreover, sensitivity of the oligoclonal pairs is altogether satisfactory.

TABLE XIII

TEST OF RECOVERY WITH DIFFERENT OLIGOCLONAL IRMA

1: 1B2 + 2B3/3C5
2: 6A3 + 2B3/3C5
3: 2B3 + 3C5 alone

Samples
1. Normal human serum + 500 pg/ml
2. Septic shock + 500 pg/ml
3. CRP + 500 pg/ml
4. Normal human serum
5. Septic shock
6. Buffer + 500 pg/ml

| | 1 | 2 | 3 |
|---|---|---|---|
| Total counts | 169671 | 170009 | 169991 |
| Standard curve | | | |
| 0 pg/ml | 793 | 654 | 664 |
| 20 pg/ml | 1071 | 1130 | 1230 |
| 50 pg/ml | 1619 | 1636 | 2272 |
| 100 pg/ml | 2531 | 2609 | 3273 |
| 200 pg/ml | 4090 | 4683 | 5580 |
| 500 pg/ml | 8405 | 10912 | 12756 |
| 1000 pg/ml | 16153 | 20010 | 23773 |
| 2000 pg/ml | 30793 | 38185 | 44540 |
| 5000 pg/ml | 63405 | 74930 | 90672 |
| % recovery | | | |
| 1 | 575 | 482 | 439 |
| 2 | 522 | 462 | 359 |
| 3 | 567 | 483 | 390 |
| 4 | 21 | 10 | 6 |
| 5 | 48 | 48 | 24 |
| 6 | 472 | 447 | 454 |
| Normal human serum | 121.8 | 107.8 | 96.7 |
| Septic shock | 110.6 | 103.4 | 79.1 |
| CRP | 120.1 | 108.1 | 85.9 |

2.5 Assay of native TNF in biological fluids with oligoclonal IRMA procedures Table XIV shows the assay of TNFα in sera or plasma or peritoneal exudates of normal subjects or subjects with septic shock. It is observed that the two oligoclonal IRMA procedures do not assay TNF in the normals, whereas they detect TNFα in the subjects with shock, this being the case both in sera and in plasma or in peritoneal exudates. The TNFα values assayed by 2B3/3C5 monoclonal IRMA being smaller.

TABLE XIV

ASSAY OF NATIVE TNF IN BIOLOGICAL FLUIDS BY OLIGOCLONAL IRMA PROCEDURES

1: 6A3 + 2B3/3C5
2: 1B5 + 2B3/3C5
3: 2B3 + 3C5

| | 1 | 2 | 3 |
|---|---|---|---|
| Total count | 162539 | 162462 | 162337 |
| Standard curve | | | |
| 0 pg/ml | 631 | 607 | 655 |
| 20 pg/ml | 1073 | 821 | 1223 |
| 50 pg/ml | 1523 | 1354 | 1761 |
| 100 pg/ml | 2561 | 2118 | 2751 |
| 200 pg/ml | 4357 | 3402 | 4966 |
| 500 pg/ml | 9555 | 7437 | 11709 |
| 1000 pg/ml | 18595 | 14088 | 22899 |
| 2000 pg/ml | 34146 | 26486 | 42713 |
| 5000 pg/ml | 68092 | 55602 | 84453 |
| 1. Normal human serum 1 | 0 | 0 | 0 |
| 2. Normal human serum 1 | 0 | 0 | 0 |
| 3. Normal human serum 2 | 0.3 | 0 | 0 |
| 4. Normal human serum 3 | 0 | 0 | 3.1 |
| 5. Normal human serum 4 | 0 | 0 | 0 |
| 6. Normal human serum 5 | 0.7 | 0 | 0 |
| 7. Normal human serum 6 | 1.4 | 2.1 | 0 |
| 8. Septic shock 1 Liège in dry tube (201 pg/ml) | 141 | 119 | 88 |
| 9. Septic shock 2 Liège in dry tube (450 pg/ml) | 1034 | 880 | |
| 10. Septic shock 3 Liège in dry tube (71 pg/ml) | 3.4 | 11 | 0.6 |
| 11. Exudate pool 1 | 33 | 26 | 14 |
| 12. Exudate pool 2 | 33 | 29 | 12 |
| 13. Septic shock 4 Liège in dry tube (+50 pg/ml) | 0 | 0 | 0 |
| 14. Septic shock 4 on EDTA | 3.7 | 0 | 0 |
| 15. Septic shock 1 on EDTA | 149 | 124 | 90 |
| 16. Septic shock 2 on EDTA | 1249 | 1175 | |
| 17. Septic shock 3 on EDTA | 2.1 | 8.5 | 0 |
| 18. Normal human serum + 500 pg/ml | 504 | 568 | 375 |
| 19. Septic shock, Ghent + 500 pg/ml | 544 | 627 | 366 |
| 20. Buffer + 500 pg/ml | 452 | 454 | 434 |

Conclusions

The pair of MAB 2B3/3C5 assays TNFα in IRMA with a high sensitivity in the culture media.

The assay of TNFα in biological fluids with the same pair of antibodies is disturbed by an interfering substance presence in the sera of normal subjects and to a greater extent in the sera of subjects with septic shock.

The interfering substance appears to bind the TNFα in a region close to the epitope recognized by the adsorbed antibody.

Other pairs of antibodies do not have this drawback, but are distinctly less sensitive and, as a result, unusable as they are for the assay of TNFα in biological fluids.

The addition of EDTA in the IRMA test decreases the effect of the interfering substance, but not completely.

The joint use of two different antibodies adsorbed on the solid phase (one responsible for sensitivity and the other insensitive to interference), and with the test carried out in the presence of EDTA, enables a sensitive IRMA to be obtained which assays TNFα in biological fluids without interference in pathological situations.

EXAMPLE VII

Development of the Assay of IL-1β

1) Immunization

Human recombinant IL-1β was used as antigen.

The immunization was carried out in rabbits using multiple intradermal injections along the vertebral column according to the method of Vaitukaitis. The injections consisted of a suspension of 50 μg of antigen dissolved in 0.5 ml of physiological fluid and 0.5 ml of Freund's complete adjuvant.

Twelve monthly boosters were performed according to the same method and with the same quantities of antigen. Blood samples were collected regularly at the marginal vein of the ear. At the end of the immunization, the rabbit was killed by total exsanguination.

The titer and the sensitivity were studied for these different bleedings. The bleedings, which showed approximately the same sensitivity and a sufficient titer, were mixed for the kinetic study at 37°, 20° and 4° C.

Pool I consists of the bleedings of the 1st and 3rd months, and pool II of the bleedings of the 4th, 5th, 6th and 7th months.

2) KINETIC STUDY

4° C. is the temperature at which the best binding of the antigen to the antibody is observed. Approximately 20% binding is attained after 24 hours and 28% after 96 hours. It can be observed that the two pools behave in parallel fashion; these different bleedings were hence mixed and approximately 180 ml of antiserum is available for use at an initial dilution of 1/8000.

3) LABELING OF THE ANTIGEN

Labeling of IL-1 by the classical chloramin T method (20 μg of chl. T-30Δ-20 μg of metabisulfite) gives an unsatisfactory result. In effect, after filtration on Sephadex G75 gel, two elution peaks are obtained.

The binding to the antibodies and the sensitivity obtained were tested with the two peaks, and it is observed that the peak I (by far the larger) binds well to the antibodies but the 200 ng of unlabeled antigen produce only an inhibition of binding of ±15%. In contrast, the peak II binds in the same manner to the antibodies, but the same quantity of antigen produces an inhibition of ±70%.

An attempt was made to improve the labeling by decreasing 10-fold the quantities of chloramine T and by eliminating the addition of metabisulfite. As shown in Table II, a further small improvement in sensitivity is achieved (80% inhibition) but the labeling efficiency is not increased; in effect, the peak I is reduced but the peak II is not increased.

An attempt was also made to improve the labeling:
1—by doubling the quantity of iodine-125;
2—by labeling with lactoperoxidase;
3—by labeling with iodogen.

While the first two methods achieve a reduction in the peak I, the peak II does not increase sufficiently to enable kits to be produced. In contrast, labeling with iodogen gives more satisfactory results. This labeling method was the one adopted. It is as follows:

iodogen (source: Pearce) is stored per 2 μg aliquot dissolved in 50 μl of chloroform;

immediately before labeling, the chloroform is evaporated off under dry nitrogen and the following are added successively into the tube:
15 μl of 0.5M PO$_4$, pH 7.5
10 μl $^{125}$I (1 mCi)
5 μg IL-1β dissolved in 25 μl 0.05M PO$_4$, pH 7.5.

The mixture is left to react for 10 minutes, shaking frequently, and the reaction is stopped by adding 500 μl of a 0.25M solution of NaI.

Nevertheless, problems are still encountered. In effect, the IL-1 dissolved in 0.05M PO$_4$ buffer does not withstand being thawed several times.

An attempt was made to store it per 30 μl aliquot, frozen or lyophilized.

It is noted that, after lyophilization, the product is completely degraded; in contrast, the fact of thawing once only seems to improve preservation.

Nevertheless, the results are not outstanding, and other buffer solutions are to be studied (Tris-HCl buffer).

Tris-HCl buffer is very suitable (100 mM Tris-HCl, pH 7.8, 0.02 mM (sic)).

4) CHARACTERISTICS OF THE ASSAY

1. Method of incubation

100 μl of standard or of sample are brought into contact with 100 μl of antiserum at an initial dilution of 1/8000, and left in contact for at least 20 hours at 4° C. 100 μl of an IL-1 solution labeled at 60,000 cpm are then added and left to react for 4 hours at room temperature, or 100 μl at 30,000 cpm for 20 hours at 4° C.

2. Specificity

The polyclonal rabbit serum shows no cross-reaction with IFNγ, IL-2 or TNFα and -β.

3. Sensitivity

The sensitivity of the assay is 10 pg/tube.

4. Comment

The tests of lyophilization of the standard, of the antiserum and of the labeled product are altogether satisfactory.

NORMAL VALUES AND METHOD OF SAMPLING

On 100 sera of normal subjects, the mean value obtained is 428±61 pg/ml.

Furthermore, the coagulation time and the effect of thawing on the serum were studied. Neither of these influences the results.

Different methods of sampling were also studied with 33 normal subjects: onto EDTA, onto citrate and onto heparin. Similar results are obtained (EDTA=344±93 pg/ml; citrate=372±121 pg/ml; heparin=352 pg/ml).

BIBLIOGRAPHIC REFERENCES (1) J. SAKLATVALA Nature Vol. 322-Aug. 7, 1986-p. 547 to 549
(2) "Mechanism of macrophage activation in RHEUMATOID ARTHRITIS, the role of IFNγ" M. G.

RIDLEY et al. in Clinical and experimental immunology 1986 Vol. 63 p. 587 to 593

(3)
- a. B. KOCK, W. REGNAT, J. Clin. Lab. Immunol. (1984), 13, 171, 178
- b. CARDENAS, MARSHALL, Journal of Immunological methods, 89 (1986) 181–189

(4) DANADERKA—The Lancet, Nov. 23, 1875, p. 1190 CACHECTIN/TUMOUR NECROSIS FACTOR (5) OPPENHEIM et al. properties of IL-1 Federation proceedings Vol. 41, No. 2, February 1982.

(6) VAITUKAITIS et al.—J. Clin. Endocrinol. Metab. 33, 988-991: 1971

(7) GREENWOOD, Biochem, J. 8: 114–120, 1963

(8) KOHLER of (sic) MILSTEIN Nature Vol. 256, 1975.

We claim:

1. A method for determining a monokine in a blood sample which comprises the following steps:
   1) stimulating a blood sample by incubating said sample for from about 2 to 4 hrs with a mitogenic agent;
   2) directly separating blood cells from said stimulated sample obtained from step (1) to give plasma containing said mitogenic agent; and
   3) determining the presence of said monokine in said plasma containing said mitogenic agent.

2. A method according to claim 1, including the additional step of combining said blood with an anticoagulant prior to said stimulating.

3. A method according to claim 2, wherein said anticoagulant is ethylenediamine tetraccetic acid, heparin or citrate.

4. A method according to claim 2, wherein said mitogenic agent is phytohemagglutinin (PHA) or a lipopolysaccharide (LPS).

5. A method according to claim 1, wherein said mitogenic agent is phytohemagglutinin (PHA) or a lipopolysaccharide (LPS).

6. A method according to claim 5, wherein said PHA is present in from about 0.02 to 50 $\mu$g/ml or said LPS is present in from about 10 to 100 $\mu$g/ml.

7. A method according to claim 6, wherein said PHA is present in from about 1 to 10 $\mu$g/ml or said LPS is present in from about 15 to 75 $\mu$g/ml.

8. A method for detecting the presence of the monokine TNF$\alpha$ or IL-1$\beta$ in a blood sample, said method comprising:
   (a) contacting a blood sample with an anticoagulant;
   (b) incubating said blood sample with a mitogenic agent for from about 2 to 4 hrs at a temperature in the range of about 4° C. to 40° C.;
   (c) directly separating said blood sample to remove blood cells and provide a plasma sample containing said mitogenic agent for assaying; and
   (d) assaying said separated plasma sample to detect the presence of said monokine.

9. A method according to claim 8, wherein said anticoagulant is ethylenediamine tetraacetic acid, heparin or citrate; and said mitogenic agent is PHA at a concentration in the range of about 0.02 to 50 $\mu$g/ml or LPS in the range of about 10 to 200 $\mu$g/ml.

10. A method according to claim 8, wherein said assaying is a displacement radioimmunoassay (RIA) assay.

11. A method according to claim 10, wherein said assay is performed with a rabbit polyclonal anti-TNF$\alpha$ or IL-1$\beta$ antiserum lacking cross-reactivity with lymphokines or other monokines.

12. A method according to claim 8, wherein said assaying is an IRMA assay.

13. A method according to claim 12, wherein at least two monoclonal antibodies recognizing different epitopes of said monokine adsorbed on a solid phase are used to bind said monokine.

14. A method according to claim 13, wherein a first adsorbed antibody is selected for sensitivity to about 10 pg/ml of monokine and a second adsorbed antibody is selected for recovery selectivity of about 100% when known values for said monokine are assayed.

15. A method according to claim 8, wherein said anticoagulant is ethylenediamine tetraacetic acid.

16. A method according to claim 8, wherein said assaying employs monoclonal antibodies with no cross-reactivity with lymphokines or other monokines.

* * * * *